United States Patent
Perry et al.

(10) Patent No.: US 8,118,867 B2
(45) Date of Patent: *Feb. 21, 2012

(54) ORBITAL IMPLANT COATING HAVING BULBOUSLY RAISED SUTURE ZONE

(75) Inventors: Arthur C. Perry, San Diego, CA (US); Roger J. Greenwald, San Diego, CA (US)

(73) Assignee: Arthur C. Perry, San Diego, CA (US)

(*) Notice: Subject to any disclaimer, the term of this patent is extended or adjusted under 35 U.S.C. 154(b) by 1071 days.

This patent is subject to a terminal disclaimer.

(21) Appl. No.: 11/726,052

(22) Filed: Mar. 21, 2007

(65) Prior Publication Data

US 2007/0191942 A1    Aug. 16, 2007

Related U.S. Application Data

(63) Continuation-in-part of application No. 10/728,066, filed on Dec. 3, 2003, now Pat. No. 7,407,510.

(51) Int. Cl.
*A61F 2/14* (2006.01)
(52) U.S. Cl. .................... 623/6.64; 623/23.75
(58) Field of Classification Search ............ 623/4.1, 623/6.64, 11.11, 23.75, 23.76
See application file for complete search history.

(56) References Cited

U.S. PATENT DOCUMENTS

| | | | |
|---|---|---|---|
| 5,713,955 A * | 2/1998 | Durette | 623/6.64 |
| 5,968,092 A * | 10/1999 | Buscemi et al. | 128/898 |
| 6,063,117 A | 5/2000 | Perry | |
| 6,248,130 B1 | 6/2001 | Perry | |
| 6,913,626 B2 * | 7/2005 | McGhan | 623/23.73 |
| 6,997,553 B2 | 2/2006 | Tung | |
| 2006/0069434 A1* | 3/2006 | Durette | 623/6.64 |
| 2006/0271185 A1 | 11/2006 | Silvestrini | |

FOREIGN PATENT DOCUMENTS

| WO | WO 9414390 A1 * | 7/1994 |
|---|---|---|
| WO | WO 9836784 A1 * | 8/1998 |

* cited by examiner

*Primary Examiner* — David H Willse
*Assistant Examiner* — Javier Blanco
(74) *Attorney, Agent, or Firm* — Charmasson, Buchaca & Leach, LLP

(57) ABSTRACT

A coating for an orbital implant where the coating has an anterior portion having a different, longer term bioabsorbability than a posterior portion. This allows the implant to have a smooth surface for insertion and to provide reduced irritation to neighboring tissues, to help prevent exposure of the porous core of the implant, and to provide a stable anchorment for extraocular muscles, but which also encourages rapid fibrovascular ingrowth. The coating is marked with a visual indicator to facilitate proper orientation. Shell materials are further selected to allow for sterile packaging, the securing of therapeutic agents thereon, and to provide adequately strong securing of the coating to the core. Apertures are formed through the coating to enhance fluid flow to and from the core, and to provide exposure of the surface of the core to extraocular muscles, and for sutures. The apertures are sized and shaped to reduce irritating surface contact with orbital tissues. In an alternate embodiment, one of the coating portions has a bulbous raised zone encompassing suture holes. The gap created between the undersurface of the raised zone and the core facilitates threading of the sutures.

25 Claims, 3 Drawing Sheets

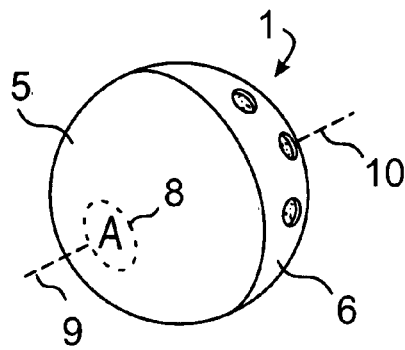
FIG. 1
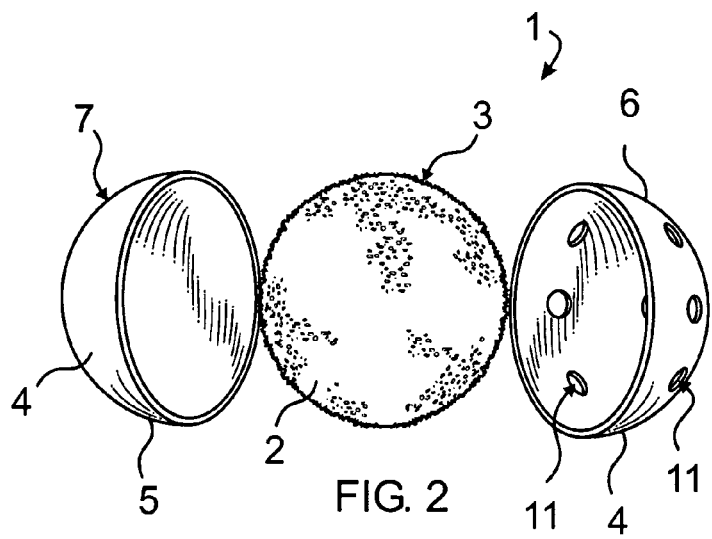
FIG. 2
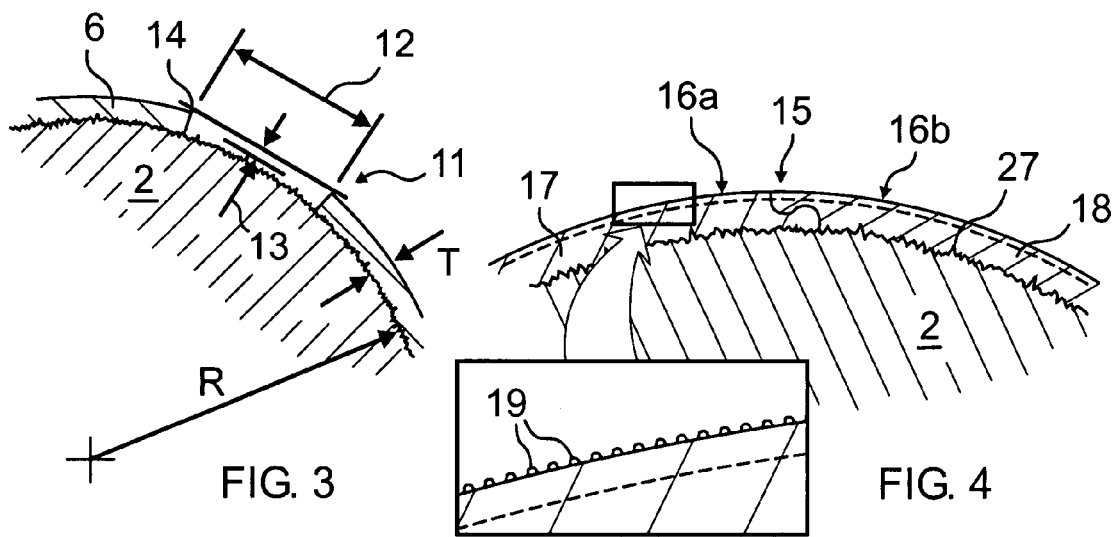
FIG. 3
FIG. 4

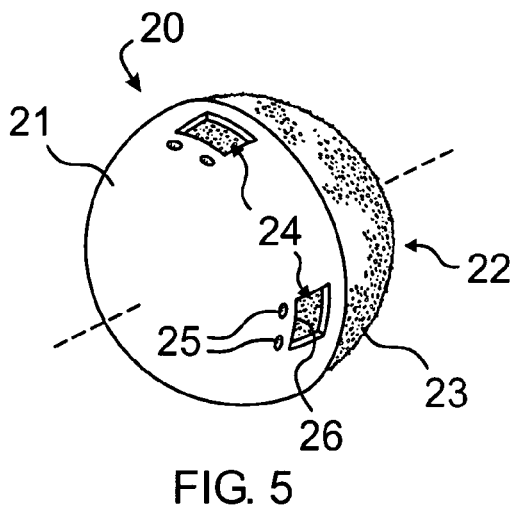
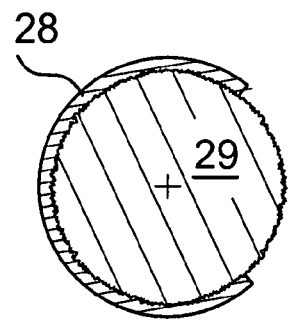
FIG. 5  FIG. 6
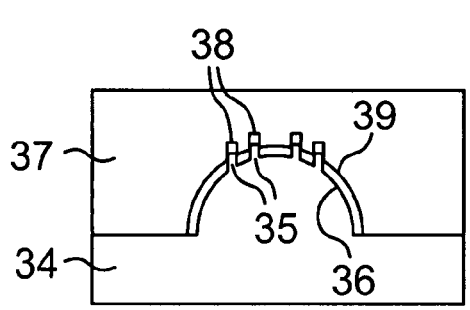
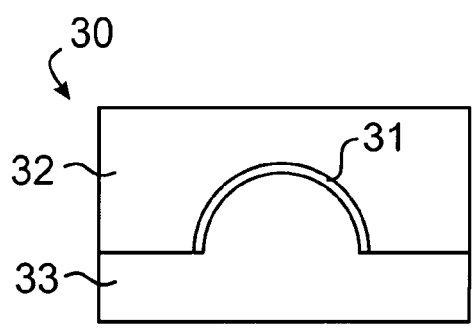
FIG. 8  FIG. 7
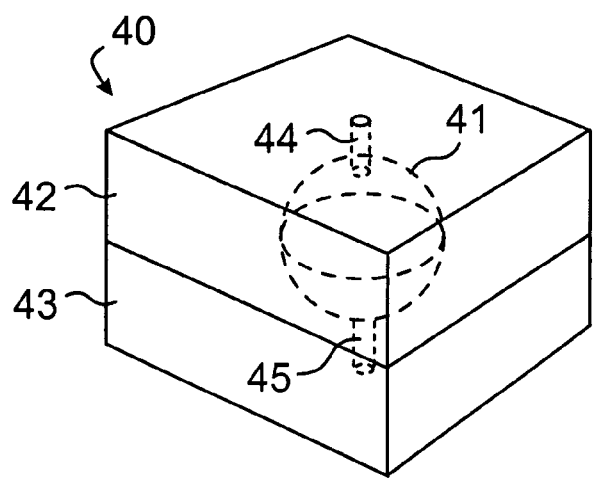
FIG. 9

ORBITAL IMPLANT COATING HAVING BULBOUSLY RAISED SUTURE ZONE

PRIOR APPLICATION

This application is a continuation-in-part of U.S. patent application Ser. No. 10/728,066 field Dec. 3, 2003 now U.S. Pat. No. 7,407,510.

FIELD OF THE INVENTION

This invention relates to orbital implants for reconstructive surgery of the socket and orbit and more particularly to materials and methods for enhancing fibrovascular ingrowth and full integration of orbital implants.

BACKGROUND OF THE INVENTION

Enucleation or evisceration of the eye is performed because of disease or trauma that make the removal of the eye, or the intraocular contents of the eye, necessary. Following such a procedure, the patient normally desires use of an artificial eye to restore a more normal appearance. To satisfactorily fit an artificial eye into the orbital socket, an orbital (herein also called an "ocular") implant must be placed within the orbit to replace the volume that was lost when the eye or its contents was removed. However, the use of an orbital implant and the subsequent fitting of the artificial eye confer more than a cosmetic benefit. They help maintain the normal structure of the eyelids and eyebrows; they aid in normal tear drainage; and, when used in children, they help stimulate normal growth of the orbital bones.

It is further known that such treatment is enhanced by encouraging fibrovascular ingrowth into porous implants so that they may become integrated as disclosed in Perry, U.S. Pat. No. 6,063,117 incorporated herein by this reference.

Porous materials such as hydroxyapatite ("HA") do have some drawbacks. Naturally derived HA exhibits surface spicules which can abrasively contact other structures within the orbit which can make insertion difficult. Further abrasion can occur after insertion, leading to the generally unwanted condition of exposure of the implant.

It has been found that a coating or wrapping of a smooth, sheet material on the outer surface of the porous core of the implant can provide a smooth surface which will facilitate deep insertion. The coating also provides a secure structure onto which the extraocular muscles may be sutured in close proximity to the implant in order to provide a good blood supply for encouraging rapid fibrovascular ingrowth. Unfortunately, such a coating can discourage rapid fibrovascular ingrowth by blocking access of bodily fluids and blood vessels to the porous core. Additionally, simply wrapping the hydroxyapatite core with such a material may present additional preparatory steps to the surgeon such that the muscle attachments may be readily affixed to the covering material and into intimate contact with the core.

It is further shown in Perry, U.S. Pat. No. 6,248,130, incorporated herein by this reference, that a coating made of bioabsorbable sheet material will allow both easy insertion and, as it degrades, allow full integration with fibrovascular tissue. The materials selected for the coating should not cause an undue adverse immune or inflammatory response and, preferably, will be rapidly bioabsorbed or penetrated by the patient's body to allow integration with fibrovascular tissue. Preferably, the coating must be made from a material which is strong enough to securely hold sutures.

Various materials have been proposed from plaster of paris to biodegradable polymeric compounds such as polyglycolic acid ("PGA"), and polylactic acid ("PLA") among others. Depending on various parameters such as its molecular morphology (crystalline vs. amorphous), hydrophobicity, and presence of additives, among others, such materials typically exhibit different rates of degradation in the body and will become bio-absorbed at different times.

This required manufacturers to weigh the benefits of a faster degrading coating which would encourage more rapid vascularization against the disadvantages of less secure muscle attachment over time, and the irritation caused by projecting spicules. Although slower degradation provides longer lasting smoothness, secure muscle attachment, and encourages epithelial cell growth if exposed, it discourages rapid fibrovascular ingrowth.

There is a need, therefore, to provide an implant that minimizes the above-described negative effects.

SUMMARY OF THE INVENTION

The principal and secondary objects of this invention are to provide an enhancement to orbital implant technology.

These and other objects are achieved by an orbital implant having a smooth, bioabsorbable coating at least partially covering a porous core. This provides a smooth surface for easy insertion and reduced irritation to neighboring tissues. In one embodiment, the coating is made to have a portion which is adapted to be bioabsorbed more rapidly than other portions, thereby encouraging rapid fibrovascular ingrowth. Another portion can be adapted to be bioabsorbed less rapidly than other portions, thereby encouraging epithelial cell growth. Optional preformed apertures through the coating enhance fluid flow to and from the core, expose the core to attached muscles, and facilitate suturing. In an alternate embodiment, a deviation of the coating from the nominal shape of the porous core may further facilitate attachment of the muscles by the creation of a clearance between the muscle attachment windows and the suture access openings. An indicia or visual indicator may be associated with the coating to facilitate proper orientation during implantation. Coating materials are selected to determine bioabsorbtion rates, to secure therapeutic agents thereon, to provide stable, secure attachment of extraocular muscles, and to provide adequately strong securing of the coating to the porous core, to allow for sterile packaging, and to provide an adequate shelf life.

BRIEF DESCRIPTION OF THE DRAWING

FIG. 1 is a diagrammatic perspective view of an orbital implant formed by a porous core covered by an outer coating having portions made from materials which are bioabsorbed by the body at different rates, and showing an orientation indicia on the outer surface of the coating.

FIG. 2 is a diagrammatic exploded perspective view of an orbital implant of FIG. 1.

FIG. 3 is a diagrammatic, partial diametrical cross-sectional view across a hole through the posterior coating portion of the implant of FIG. 1.

FIG. 4 is a diagrammatic, diametrical cross-sectional view of the bioabsorbable coating according to the invention having portions bonded by a snap fit structure and a zoomed-in view of surface microtexturing.

FIG. 5 is a diagrammatic perspective view of an alternate orbital implant having a coating covering only the anterior hemisphere of the implant.

FIG. 6 is a diagrammatic, cross-sectional view of an alternate embodiment of the invention having a hyper-hemispherically shaped, single material coating.

FIG. 7 is a diagrammatic, cross-sectional view of a die press for forming a coating according to the invention.

FIG. 8 is a diagrammatic, cross-sectional view of an alternate embodiment of a die press for forming a coating according to the invention.

FIG. 9 is a diagrammatic, perspective partial see-through view of a mold for injection molding an implant if FIG. 1.

DESCRIPTION OF THE PREFERRED EMBODIMENT OF THE INVENTION

Figure 10:
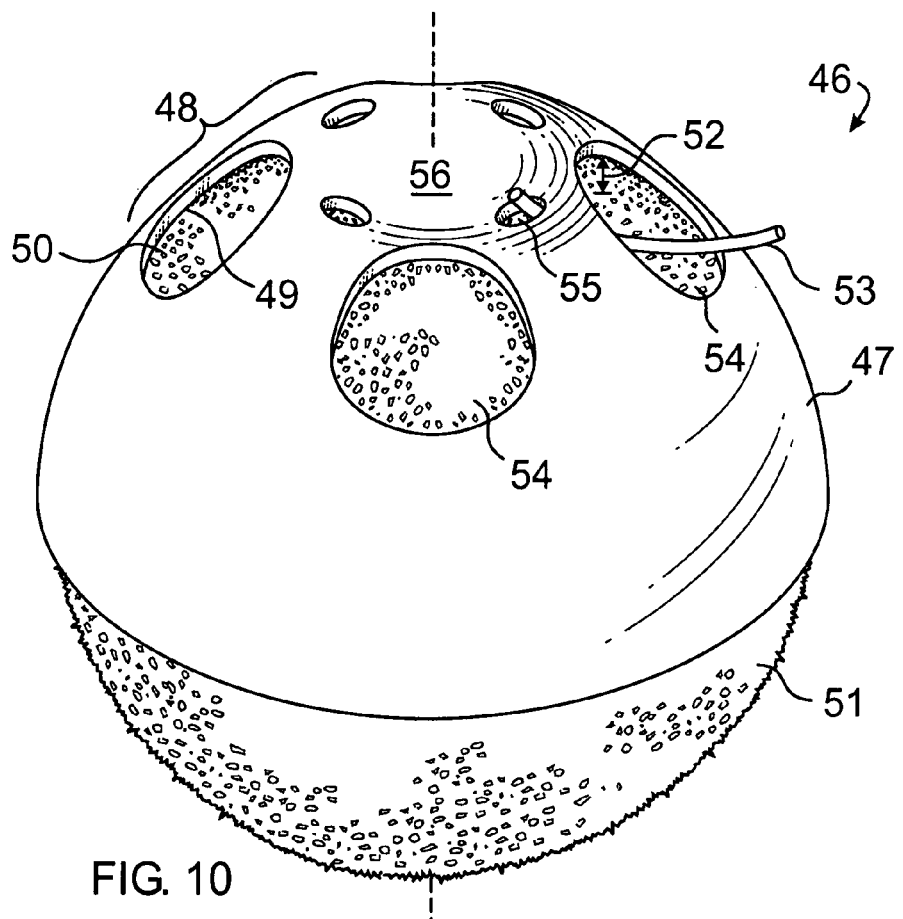
FIG. 10 is a diagrammatic, perspective view of an alternate embodiment of an orbital implant having a coating having a bulbous raised zone.

Although the preferred embodiment of the invention will be described as it applies to a substantially spherical hydroxyapatite core, those skilled in the art will readily appreciate application of the invention to implants having different shapes and cores made from different materials.

Referring now to the drawing, there is shown in FIGS. 1 and 2, an orbital implant 1 formed by a substantially spherical porous body or core 2 sized to fill the orbit in approximation of a natural eyeball in a mammalian patient. The core is preferably made from a porous material such as naturally derived porous hydroxyapatite ("HA"). Other materials which can be used include porous synthetic HA, porous aluminum oxide, porous zirconium, porous polyethylene, porous poly-urethane, and other biocompatible porous materials capable of fibrovascular ingrowth.

The arcuate, substantially spherical outer surface 3 sections of the core are at least partially covered by a coating 4 having a first arcuate, substantially hemispherical anterior portion 5 and a second arcuate, substantially hemispherical posterior portion 6 sized and shaped to intimately fit over a substantial portion of the outer surface of the implant. The coating has an outer surface 7 which is smoother than the outer surface 3 of the implant 2. Preferably, the anterior portion 5 is selected from a material or materials so that its bioabsorbability or degradation rate is slower than that of the posterior portion 6.

Because of the different bioabsorbability of various portions of the coating, it is important for the ocular surgeon to properly identify and orient those portions during surgery. Easy identification is accomplished by including one or more identifying indicium on the outer surface of the coating. An indicia can include graphics, such as coloring, or even a graphical depiction of an eye, or lettering alone or to form words such as "anterior", "posterior", "front", or "back". The indicia is imprinted or embossed on the outer surface of the implant 1. Positioning of the lettering such as the letter "A" for "anterior" in a zone 8 on the anterior-most pole 9 of the implant and a "P" for posterior (not shown) on the opposite pole 10 of the implant is an example. Such lettering can be formed by an indentation in the thickness of the coating, or in ink or dye selected from commercially available, government approved (such as by the United States Food and Drug Administration or "FDA"), biocompatible inks and dyes. Alternately, indicia can be through color coding. For example, the anterior and posterior portions can be colored differently. Government approved biocompatible dyes are added during manufacturing to the material feedstock of the respective coating portions. Alternately, physical treatment of the outer surface regions of the coating such as the location of windows, or otherwise differently textured regions can be used as an orientation indicia.

The anterior portion 5 material is selected to have a bioabsorbability property such as a degradation rate of about 6 months or longer, more preferably about one year or longer, and most preferably about 1.5 years or longer. The selected material is strong enough to hold a suture until degradation or removal of the suture, or for a period of time sufficient to allow attachment of the muscle directly to the implant through ingrowth. The coating is also sufficiently plastic to allow cutting of windows during surgery with a knife or cautery or during the manufacturing process by any number of means known to those skilled in the art to expose the core for the attachment of the extraocular muscles. Preferably, the coating will allow penetration of a suturing needle interoperatively without fracturing. However, penetrability can be enhanced by providing suture holes described below. The anterior material is sufficiently rigid to maintain a sutured extraocular muscle under common tension forces directly against the implant.

The anterior portion 5 is preferably made from a polymeric bioabsorbable material such as polyglycolic-based materials, polylactic-based materials or combinations thereof. Such materials can include, but are not limited to, polyglycolic acid ("PGA"), polylactic acid ("PLA"), polycaprolacitone, polydiox-anone, polycyanoacrylate, polyothoester, poly(gamma-ethyl glutamate), and pseudo-poly (amino acid).

Various parameters of this material are selected or adjusted to determine its bioabsorbability or degradation rate. The parameters can including but are not limited to its hydrophobicity, cross-linking, morphology (crystalline vs. amorphous), melt and glass-transition temperatures, molecular weight, molecular weight distribution, end groups, sequence distribution (random vs. blocky), the presence and condition of monomer or additives, the presence of hydrolytically unstable linkages along the backbone created with chemical functional groups such as esters, anhydrides, orthoesters, and amides.

The anterior portion material parameters are selected, generally, to provide a slower rate of degradation or bioabsorbability by increasing one or more of the following parameters: crystalline morphology, molecular weight, hydrophobic properties, and the lactide content of the material is preferably polylactide or poly(ε-caprolactone).

Referring now to the parameters of the posterior portion 6, those parameters are selected, generally, to provide an increased rate of degradation or bioabsorbability over that of the anterior portion. Achieving faster bioabsorbability is accomplished by increasing one or more of the following parameters: adding modified acid endgroups, selecting a more amorphous morphology, increasing hydrophilic properties, increasing the number of hydrolytically unstable bonds, decreasing molecular weight, decreasing cross-linkages, increasing glycolide content.

The posterior material is most preferably selected from polyglycolide or amorphous 50/50 DL-lactide-co-glycolide. In this way, the posterior portion preferably degrades between about one day and four months, more preferably between about one day and eight weeks, and most preferably between about one day and six weeks.

Most preferably, the thickness of the coating for both portions is substantially the same to maintain adequate surface uniformity and smoothness, and adequate sphericity for spherically shaped implants, and to maintain uniformity in manufacturing. The coating is, therefore, preferably less than 2.0 millimeters thick, more preferably less than 1.0 millimeter thick, and most preferably less than 0.5 millimeter thick.

The material and coating thickness are most preferably selected to allow the easy burning or cutting of apertures such as passageways, windows or other holes through the coating using a fine tipped, high temperature (>1093° C. or >2000° F.) battery operated handheld cautery, such as AARON MEDICAL COMPANY catalog No. AA01 cauterizing tool which is commercially available from the Aaron Medical Company of North Saint Petersburg, Fla.

In order to further enhance immediate fluid flow into and out of the porous core for rapid fibrovascular ingrowth, a number of passageways 11 are manufactured into the posterior portion 6 of the coating. The passageways can be formed at the time the coating is molded or later machined or otherwise formed into the coating during or after molding and/or after placement on the core. The passageways are shaped, sized and located to afford maximum fluid exchange between the core and surrounding tissues of the orbit without allowing interference from any underlying core surface spicules during implantation. The passageways are preferably uniformly spaced apart and restricted to the posterior portion 6 of the coating. Also, to maintain the structural integrity of the coating near where the extraocular muscle suturing will occur, the passageways are located a distance apart from these regions. It should be understood that the passageways need not extend fully through the coating, but can be cylindrical depressions where the coating is thinner. Although, bioabsorbtion may take longer, such depressions may be more economically manufactured.

Referring now to FIG. 3, each passageway 11 is preferably circular having a diameter 12 selected so that a radial buffer distance 13 exists between the outermost extent of the outer surface of the core 2 in communication with the passageway, and the upper lip or rim 14 of the passageway. Those skilled in the art will no doubt recognize that the passageway diameter 12 is of course dependent on the radius R of the core and the thickness T of the coating. It has been found that the buffer distance 13 be preferably between about 100 and 200 millimeters, more preferably between about 0.05 and 0.15 millimeters and most preferably between about 0.025 and 0.075 millimeters. Based on typical ranges for implant sizes for humans, and the preferred coating thickness ranges described above, passageway diameters should be preferably between about 1.0 and 3.0 millimeters, more preferably between about 1.5 and 2.5 millimeters, and most preferably between about 1.5 and 2.0 millimeters. To maintain structural integrity the passageway centers are preferably spaced-apart by between about 3 and 6 millimeters, more preferably between about 3 and 5 millimeters and most preferably between about 3 and 4 millimeters.

The two dissimilar portions of the coating are bonded together using any of a number of bonding techniques or types applicable to the materials used. Examples include glued bonds, chemical bonds, molecular bonds, magnetic bonds, electrostatic bonds, ultrasonic welds, heat welds, press fittings, snap fittings, shrink fittings, friction fittings, and mechanically fastened bonds. A snap fitting type bond 15 is shown in FIG. 4. In this way, the coating may be supplied separately and attached to the core just prior to implantation.

The core and coating are preferably pretreated to contain various therapeutic agents to help control cell adhesion, migration, proliferation, and differentiation, and to provide a means for reducing an adverse immune response in the patient. Therapeutic agents can include but are not limited to antibiotic agents, anti-inflammatory agents, vascularization promoting agents growth factors, cell adhesion modulating molecules, and gene fragment agents, immuno-suppressants, wound-healing promoters, blood-clot dissolving agents, blood-clotting agents, and any combination thereof. These compounds and conveyance vehicles are well described in Perry, U.S. Pat. No. 6,248,130, incorporated herein by this reference.

Alternately, the anterior portion can be selectively treated to encourage epithelial cell growth and collagen formation. Further, the outer surface 16a of the anterior portion 17 and/or the outer surface 16b of the posterior portion 18 of the coating may be modified to encourage cellular adhesion and/or proliferation. Modification can include local change of the surface material parameters discussed above, local placement of therapeutic agents, and/or microtexturing 19 of the outer surface which can include, but are not limited to indentations, perforations, or other microstructures such as raised bumps or ridges which are most preferably dimensioned to be between about 2 and 5 microns in size. Alternately, the surface energy can be manipulated to enhance biocompatibility such as through changing its surface energy. In this way different portions of the implant are modified to selectively encourage different types of tissue growth. Further, this can create two concentrically adjacent layers, shown separated by the dashed line in FIG. 4, where one layer has a material not present in the other layer.

Referring now to FIG. 5, an alternate embodiment of the implant 20 according to the invention for those situations demanding the maximum capability for stimulating rapid ingrowth, the coating 21 is formed to have an anterior portion which is bioabsorbed slowly and little or no portion of the coating covers to posterior side 22 of the implant 23. As is true with any of the embodiments, windows 24 can be preformed into the anterior portion of the coating in the approximate location for extraocular muscle attachment. Each window also has preformed suture holes 25 located near the anterior edge 26, and the anterior coating may be locally deformed such as to create a passageway between the windows and suture holes. The coating is held in place by a friction bond formed by spicules 27 penetrating into, deforming, and thereby intimately contacting the coating portion 18 as shown in FIG. 4. Alternately, further securement of the coating 28 upon the core 29 may be accomplished by shaping it into a hyper-hemispherical shape as shown in FIG. 6.

Referring now to FIG. 7 there will be described the preferred manufacturing process for creating an orbital implant embodying the above-features.

A stamping die pair 30 is selected having a substantially hemispherical inner chamber 31. The chamber is constructed to have an inner diameter that is selected to be between about 100 to 1000 microns larger than the diameter of the HA core to which the coating will be secured. The die pair splits into a top, outer surface creating die portion 32 and a bottom, inner surface creating die portion 33. A sheet of a first type of polymer, is selected to form the anterior portion of the coating, and heated to allow a degree of plastic deformation. The sheet is loaded into the die and stamped under a pressure, temperature and time sufficient to overcome resiliency in the sheet material to form a first anterior portion of the coating.

The posterior portion is formed using a similar stamping die pair. A sheet of a second type of polymer which degrades faster than the first type is selected, and is preferably colored with a dye having sufficient contrast from the first sheet, and stamped to form the posterior portion of the coating.

The two hemispherically shaped coating portions are then mated around the appropriately sized HA core, and bonded to one another along their common equator using an ultrasonic weld.

The entire implant is then packaged in a moisture- and light-proof pouch and sterilized by subjecting it to gamma or electron beam radiation.

Referring now to FIG. 8, apertures can be molded into the coating by adapting the stamp die pair so that the bottom die 34 has a number of substantially cylindrical projections 35 extending vertically upwardly from the top surface 36. Each projection is sized, shaped and located to form a desired aperture. The top die 37 has correspondingly shaped, sized and located holes 38 allowing intimate penetration of the projections when the dies are brought together. The remainder of the lower, outer surface 39 of the upper die is etched to form valleys which correspond to the microtexturing desired on the surface of the intended portion of the coating. Projections of other shapes corresponding to the extraocular muscle windows and suture holes can be placed where desired. The projections penetrating the holes will punch out material from the polymer sheet to form the desired apertures in the coating.

Referring now to FIG. 9, there will be described an alternate manufacturing process for creating an orbital implant embodying the above-features.

A substantially spherical porous hydroxyapatite implant is selected having a given diameter and placed in a mold 40 having a spherical inner chamber 41. The chamber is constructed to have an inner diameter that is selected to be between about 100 to 1000 microns larger than the diameter of the implant and splits into a top hemisphere 42 and a bottom hemisphere 43. The bottom hemisphere as a number of cylindrical projections extending radially inwardly from the inner surface. Each projection is sized, shaped and located to form a desired passageway. The remainder of the inner surface is etched to form valleys which correspond to the texturing desired on the posterior portion of the coating. The top hemisphere can have additional projections corresponding to the extraocular windows and suture holes.

Two types of liquid polymer, each selected respectively for the anterior and posterior portions of the coating, are injected into ports 44, 45 at the poles of each hemisphere. The two types of polymer preferably contain two different dyes which readily distinguish the portions. The liquid polymer has a viscosity which allows it to partially penetrate the pores of the implant thereby forming a mechanical bond once the polymers have hardened. The projections obstruct flow of the fluid to form the desired passageways. The two polymers meet along the equator and intermix to form a molecular bond between the two coating portions.

After hardening, the mold is separated and the implant removed. The implant and coating are sterilized using a flow of ethylene oxide gas and packaged in a moisture- and light-proof pouch. Care should be taken during sterilization not to adversely affect and therapeutic agents present.

Alternately, a first top hemisphere of the mold intended for the anterior portion of the coating is sized to form a coating portion that is 100 microns thick, while the bottom hemisphere is sized to form a coating portion that is 200 microns thick. A first injection is made similar to that described above. The polymer selected for the anterior portion includes adhesion factor and growth factor therapeutic agents to encourage epithelial cell attachment and fibrovascular tissue growth. After hardening, the first top hemisphere of the mold is replaced with a second top hemisphere sized to form a coating portion which is 200 microns thick. A second injection is then made into the top of the mold using a faster degrading polymer similar to the polymer used to form the posterior coating portion. This polymer includes an antibiotic therapeutic agent bond to the polymer molecule. After hardening, the implant now has a uniformly thick coating of 200 microns. However, the anterior coating portion has two concentrically adjacent layers formed from two different materials. Those skilled in the art will appreciate that different polymers or differently treated polymers may be used to form the layers.

Alternately, two hemispherical coating portions are separately molded to form hollow hemispheres. The hemispheres are then ultrasonically welded to each other along their mutual equator and around an appropriately sized implant. During welding some polymer renters a liquid phase and flows into adjacent pores in the core, which rehardens to form a mechanical bond thereto.

It should be understood that the coating portions may be molded to have uniform thickness and then later machined to form the passageways, windows, and/or holes.

Referring now to FIG. 10, there is shown an alternate embodiment 46 of the orbital implant, wherein one of the portions 47 of the external coating has a bulbous raised zone 48 whose undersurface 49 separates from the outer surface 50 of the core 51. The major portion of that undersurface being spaced apart from the core creates a gap 52 that facilitates the threading of sutures 53 through passageways or windows 54 and suture holes 55 cut through the coating section, similar to those of the first described embodiments shown in FIGS. 1-5. The maximum width of the gap 52 at the apex 56 of the bulbous zone 48 need not exceed 0.5 millimeter in order to accommodate the sutures.

Figure 11:
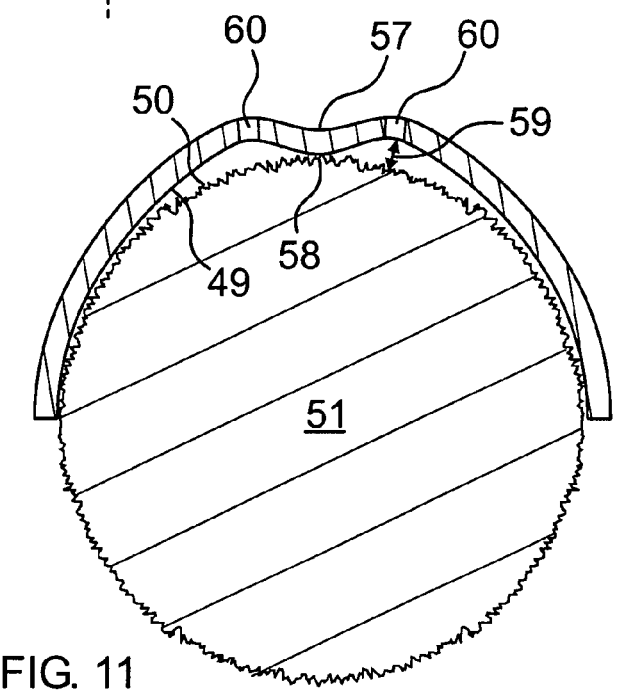
FIG. 11 is a diagrammatic, cross-sectional view of an alternate embodiment of an orbital implant having a coating having a apical ring-shaped bulbous raised zone.

Alternately, as shown in FIG. 11, the apex of the bulbous zone can be formed to have an apical dimple 57 so that the undersurface 49 of the external coating contacts the outer surface 50 of the core 51 to form an additional support 58 for the vaulting of an apical ring-shaped gap 59. In this embodiment, the suture holes 60 are located at the maximum width of the gap.

EXAMPLE

Enucleation: A standard enucleation is done including tagging of the extraocular muscles with bioabsorbable suture. The orbit is sized, using a set of sizing spheres, to determine the size of the implant to be used. An implant is of the proper size when it is the largest implant that can be placed deep into the orbit without creating tension on the overlying tissues and while allowing adequate room for an artificial eye of sufficient thickness.

Once the desired size of the implant has been determined, a sterile marking pen is used to draw the location of the muscle windows on the anterior polymer. The muscle windows are most easily cut by using a fine tipped, high temperature (>1093° C. or >2000° F.) battery operated handheld cautery and by cutting the coating material along the previously drawn lines. The remaining small pieces of polymer inside the windows can then be removed with forceps. In a similar manner suture exit holes may be formed in proximity to the windows. The suture from the tagged muscles are passed through the windows and exit through the suture holes where they are then tied together. An optional step to aid the passage of the suture needle is to use a 25 or 27-gauge hypodermic needle to create a tunnel from the suture exit hole to the muscle window. Additionally, a number of small holes (8-10) are made using the cautery near the posterior pole of the implant. This allows for an antibiotic and local anesthetic mixture that is infused into the hydroxyapatite core to flow into the posterior orbit. These holes also serve as areas for rapid blood vessel in-growth.

The Coated Bio-eye HA Orbital Implant should then be soaked in an antibiotic and local anesthetic solution after the widows for the muscle attachments and posterior holes have been made. This is done just prior to implantation.

Eviseration: A standard evisceration is done with or without removal of the cornea. Sizing spheres are used to determine the size of the implant to be used. Once the proper implant has been chosen, muscle windows may or may not be formed in the anterior polymer hemisphere. Multiple (8-10) small holes are made in the posterior polymer hemisphere. The implant is then soaked in an antibiotic and local anesthetic solution. The implant is placed in the scleral cavity with the amber colored, or otherwise indicated, anterior hemisphere toward the conjunctiva and the purple colored, or otherwise indicated, hemisphere toward the optic nerve. Anterior and posterior relaxing incisions may be used in the quadrants between the extraocular muscles to allow deeper placement of the implant in the orbit, to help reduce tension on the anterior scleral closure, and to allow the use of a larger implant than is otherwise possible. Scleral windows measuring approximately 3×7 millimeters may also be cut just posterior to the extraocular muscle insertion. These scleral windows provide additional contact between the implant and the highly vascular tissues of the orbit, thereby accelerating the rate of vascular ingrowth.

While the preferred embodiment of the invention has been described, modifications can be made and other embodiments may be devised without departing from the spirit of the invention and the scope of the appended claims.

What is claimed is:

1. An orbital implant which comprises:
   a substantially spheroid porous material core comprising an outer surface;
   an anterior first, non-liquid, bioabsorbable, solid material external coating portion covering a first outer surface section of said core and having a thickness of less than 2.0 millimeters;
   said first coating portion being made from a material capable of carrying a suture at said thickness and having a first bioabsorbability rate;
   a second, non-liquid, solid material external coating portion, distinct from said first portion, covering a second outer surface section of said core; said second coating portion having a second bioabsorbability rate different from said first bioabsorbability rate;
   wherein said first coating portion comprises at least one bulbously raised zone having an undersurface spaced apart from said outer surface of said core to form a gap sized to accommodate a suture;
   wherein said bulbously raised zone is positioned on an anterior location of said implant and has passageways cut through said first coating portion to accommodate a sutures; and,
   wherein said first coating portion is deformed to intimately contact surface features on said core.

2. The implant of claim 1, wherein said coating portion comprises a surface having microtexturing.

3. The implant of claim 2, wherein said microtexturing comprises a plurality of microstructures selected from the group consisting of indentations, perforations, bumps and ridges.

4. The implant of claim 1, wherein said first coating portion comprises an agent selected from the group consisting of therapeutic agents and immunosuppressant agents.

5. The implant of claim 4, wherein said therapeutic agent is selected from the group consisting of a vascularization agent, and antibiotic agent, an immuno-suppressant, a wound-healing promoter, a blood-clot dissolving agent, a blood-clotting agent, a cell-adhesion modulating molecule, and any combination thereof.

6. The implant of claim 1, wherein said first and second coating portions are bonded to one another along a bond.

7. The implant of claim 6, wherein said bond is selected from the group consisting of:
   glued bonds, chemical bonds, molecular bonds, magnetic bonds, electrostatic bonds, ultrasonic welds, heat welds, press fittings, snap fittings, shrink fittings, friction fittings, and mechanically fastened bonds.

8. The implant of claim 1, wherein said thickness is selected to allow melting penetration using a handheld cautery.

9. The implant of claim 1, which further comprises an indicia identifying said first coating portion.

10. The implant of claim 9, wherein said indicia comprises a marking selected from the group consisting of lettering and a color coding.

11. The implant of claim 1, wherein at least one of said coating portions has a passageway therethrough.

12. The implant of claim 11, wherein said passageway is positioned on a posterior location of said implant.

13. The implant of claim 11, wherein said passageway is sized to allow fluid exchange therethrough.

14. The implant of claim 11, wherein said passageway has an upper rim at the surface of said at least one of said coating portion, and a portion of said core extends into said passageway up to a buffer distance from said upper rim.

15. The implant of claim 1, wherein said first coating portion comprises two concentrically adjacent layers wherein a first of said layers comprises a material not present in a second of said layers.

16. The implant of claim 1, wherein said thickness is less than one millimeter.

17. The implant of claim 1, wherein said zone is ring-shaped.

18. The implant of claim 17, wherein said zone surrounds an dimple.

19. An artificial eye which comprises:
    an orbital implant comprising a substantially spheroid porous material core having an outer first surface;
    a coating at least partially covering said outer first surface;
    said coating having a thickness of less than 2.0 millimeters;
    said coating having a first, non-liquid, bioabsorbable, solid material, exposed portion having a first bioabsorbability rate and a separate second, non-liquid, solid material, exposed portion, distinct from said first portion, having a second bioabsorbability rate different from said first bioabsorbability rate;
    wherein one of said coating portions comprises at least one bulbously raised zone having an undersurface spaced apart from said outer first surface to form a gap sized to accommodate a suture;
    wherein said bulbously raised zone is positioned on an anterior location of said artificial eye and has passageways cut through said coating portion to accommodate sutures; and,
    wherein said first coating portion is deformed to intimately contact surface features on said core.

20. The artificial eye of claim 19 wherein said coating has an outer second surface which is smoother than said first surface.

21. An orbital implant comprising:
    a substantially spheroid porous material body sized and shaped to be placed in the orbit, said substantially spheroid body comprising an outer surface;

a coating covering a section of said outer surface of said substantially spheroid body; said coating having a thickness of less than 2.0 millimeters;

wherein said coating has a first, non-liquid, bioabsorbable, solid material, exposed portion having a first bioabsorbability rate and a separate second, non-liquid, solid material, exposed portion, distinct from said first portion, having a second bioabsorbability rate different from said first bioabsorbability rate;

wherein one of said coating portions comprises at least one bulbously raised zone having an undersurface spaced apart from said outer surface of said substantially spheroid body to form a gap sized to accommodate a suture;

wherein said bulbously raised zone is positioned on an anterior location of said orbital implant and has passageways cut through said coating portion to accommodate sutures; and, wherein said first coating portion is deformed to intimately contact surface features on said porous material body.

22. The implant of claim 21, wherein said coating comprises an immunosuppressant agent.

23. The implant of claim 21, wherein said coating comprises a therapeutic agent.

24. The implant of claim 21, wherein said coating comprises a surface having microtexturing.

25. A combination of an orbital implant and a coating for implantation into the orbit of a mammal;

said orbital implant comprises a porous material body having an arcuate outer surface;

said coating comprises:

a first, non-liquid, bioabsorbable, solid material, external portion being made from a first material having a first bioabsorbability property;

said first portion covering a first section of said arcuate outer surface;

said first portion having a thickness of less than 2.0 millimeters:

a second, non-liquid, solid material, external portion, separate and distinct from said first portion, being made from a second material having a second bioabsorbability property;

said second portion covering a second section of said arcuate outer surface;

wherein said first bioabsorbability property is different from second bioabsorbability property;

wherein one of said coating portions comprises at least one bulbously raised zone having an undersurface spaced apart from said arcuate outer surface to form a gap sized to accommodate a suture;

wherein said bulbously raised zone is positioned on an anterior location of said orbital implant and has passageways cut through said coating portion to accommodate sutures; and, wherein said first coating portion is deformed to intimately contact surface features on said porous material body.

* * * * *